US008140148B2

(12) United States Patent
Crowley

(10) Patent No.: US 8,140,148 B2
(45) Date of Patent: *Mar. 20, 2012

(54) READABLE PROBE ARRAY FOR IN VIVO USE

(75) Inventor: Robert J. Crowley, Sudbury, MA (US)

(73) Assignee: Boston Scientific Scimed Ltd., Maple Grove, MN (US)

( * ) Notice: Subject to any disclaimer, the term of this patent is extended or adjusted under 35 U.S.C. 154(b) by 1110 days.

This patent is subject to a terminal disclaimer.

(21) Appl. No.: 11/621,415

(22) Filed: Jan. 9, 2007

(65) Prior Publication Data

US 2007/0167719 A1    Jul. 19, 2007

Related U.S. Application Data

(63) Continuation of application No. 09/881,283, filed on Jun. 14, 2001, now Pat. No. 7,302,289, which is a continuation of application No. 09/233,409, filed on Jan. 19, 1999, now Pat. No. 6,289,229.

(60) Provisional application No. 60/071,906, filed on Jan. 20, 1998.

(51) Int. Cl.
*A16B 6/00* (2006.01)

(52) U.S. Cl. .......... 600/478; 600/317; 600/476

(58) Field of Classification Search .......... 600/317, 600/407, 476, 478
See application file for complete search history.

(56) References Cited

U.S. PATENT DOCUMENTS

| | | |
|---|---|---|
| 2,002,559 A | 5/1935 | Wappler |
| 2,583,937 A | 1/1952 | Fossati |
| 3,176,114 A | 3/1965 | Kneisley |
| 4,233,493 A | 11/1980 | Nath |
| 4,274,706 A | 6/1981 | Tangonan |
| 4,289,966 A | 9/1981 | Roberts |
| 4,340,307 A | 7/1982 | Diamond et al. |
| 4,472,728 A | 9/1984 | Grant et al. |
| 4,541,272 A | 9/1985 | Bause |
| 4,548,505 A | 10/1985 | Ono |
| 4,556,057 A | 12/1985 | Hiruma et al. |
| 4,560,286 A | 12/1985 | Wickersheim |
| 4,570,638 A | 2/1986 | Stoddart et al. |
| 4,578,061 A | 3/1986 | Lemelson |
| 4,652,517 A | 3/1987 | Scholl et al. |

(Continued)

FOREIGN PATENT DOCUMENTS

CA    2093735 A1    10/1993

(Continued)

OTHER PUBLICATIONS

Anidjar, et al., "Ultraviolet Laser-Induced Autofluorescence Distinction Between Malignant and Normal Urothelial Cells and Tissues," *Journal of Biomedical Optics* 1(3):335-341 (1996).

(Continued)

*Primary Examiner* — Brian Casler
*Assistant Examiner* — Christopher Cook
(74) *Attorney, Agent, or Firm* — Finnegan, Henderson, Farabow, Garrett & Dunner L.L.P.

(57) ABSTRACT

A disposable high-density, optically readable polydeoxynucleotide array with integral fluorescence excitation and fluorescence emission channels is described. The compact array size allows integration into several types of interventional devices such as catheters, guidewires, needles, and trocars and may be used intraoperatively. Highly sensitive monitoring of the metabolic and disease pathways of cells in vivo under varying chemical, genetic, and environmental conditions is afforded.

65 Claims, 7 Drawing Sheets

U.S. PATENT DOCUMENTS

| | | | |
|---|---|---|---|
| 4,670,380 A | 6/1987 | Dattagupta |
| 4,672,972 A | 6/1987 | Berke |
| 4,718,417 A | 1/1988 | Kittrell |
| 4,743,534 A | 5/1988 | Pham |
| 4,770,992 A | 9/1988 | Van den Engh et al. |
| 4,774,191 A | 9/1988 | Khanna et al. |
| 4,803,992 A | 2/1989 | Lemelson |
| 4,813,790 A | 3/1989 | Frankel |
| 4,824,776 A | 4/1989 | Heller et al. |
| 4,832,034 A | 5/1989 | Pizziconi et al. |
| 4,872,458 A | 10/1989 | Kanehira et al. |
| 4,882,269 A | 11/1989 | Schneider et al. |
| 4,882,623 A | 11/1989 | Uchikubo |
| 4,894,547 A | 1/1990 | Leffell et al. |
| 4,895,156 A | 1/1990 | Schulze |
| 4,898,175 A | 2/1990 | Noguchi |
| 4,902,896 A | 2/1990 | Fertig, Sr. et al. |
| 4,925,268 A | 5/1990 | Iyer et al. |
| 4,928,172 A | 5/1990 | Uehara et al. |
| 4,930,516 A | 6/1990 | Alfano et al. |
| 4,938,602 A | 7/1990 | May et al. |
| 4,981,138 A | 1/1991 | Deckelbaum et al. |
| 4,987,065 A | 1/1991 | Stavrianopoulos et al. |
| 4,996,143 A | 2/1991 | Heller et al. |
| 5,000,901 A | 3/1991 | Iyer et al. |
| 5,001,556 A | 3/1991 | Nakamura et al. |
| 5,009,655 A | 4/1991 | Daignault, Jr. et al. |
| 5,021,888 A | 6/1991 | Kondou et al. |
| 5,034,010 A | 7/1991 | Kittrell et al. |
| 5,036,853 A | 8/1991 | Jeffcoat et al. |
| 5,037,615 A | 8/1991 | Kane |
| 5,042,494 A | 8/1991 | Alfano |
| 5,045,056 A | 9/1991 | Behl |
| 5,056,503 A | 10/1991 | Nagasaki et al. |
| 5,062,428 A | 11/1991 | Chance |
| 5,082,630 A | 1/1992 | Partin et al. |
| 5,106,387 A | 4/1992 | Kittrell et al. |
| 5,109,126 A | 4/1992 | Agrawal et al. |
| 5,115,137 A | 5/1992 | Andersson-Engels et al. |
| 5,116,759 A | 5/1992 | Klainer et al. |
| 5,125,404 A | 6/1992 | Kittrell et al. |
| 5,127,407 A | 7/1992 | Tan |
| 5,131,398 A | 7/1992 | Alfano et al. |
| 5,143,066 A * | 9/1992 | Komives et al. ............ 600/317 |
| 5,166,755 A | 11/1992 | Gat |
| 5,166,990 A | 11/1992 | Riccitelli et al. |
| 5,172,693 A | 12/1992 | Doody |
| 5,174,297 A | 12/1992 | Daikuzono |
| 5,187,572 A | 2/1993 | Nakamura et al. |
| 5,187,672 A | 2/1993 | Chance et al. |
| 5,188,934 A | 2/1993 | Menchen et al. |
| 5,193,542 A | 3/1993 | Missanelli et al. |
| 5,194,393 A | 3/1993 | Hugl et al. |
| 5,197,470 A | 3/1993 | Helfer et al. |
| 5,201,318 A | 4/1993 | Rava et al. |
| 5,206,174 A | 4/1993 | Gehrke et al. |
| 5,213,569 A | 5/1993 | Davis |
| 5,225,326 A | 7/1993 | Bresser et al. |
| 5,233,621 A | 8/1993 | Lawandy |
| 5,242,437 A | 9/1993 | Everett et al. |
| 5,256,535 A | 10/1993 | Ylikoski et al. |
| 5,261,410 A | 11/1993 | Alfano et al. |
| 5,262,645 A | 11/1993 | Lambert et al. |
| 5,304,173 A | 4/1994 | Kittrell et al. |
| 5,305,748 A | 4/1994 | Wilk |
| 5,309,907 A | 5/1994 | Fang et al. |
| 5,318,024 A | 6/1994 | Kittrell et al. |
| 5,344,784 A | 9/1994 | Attridge |
| 5,348,018 A | 9/1994 | Alfano et al. |
| 5,350,375 A | 9/1994 | Deckelbaum et al. |
| 5,351,532 A | 10/1994 | Hager |
| 5,370,998 A | 12/1994 | Crawford et al. |
| 5,377,676 A | 1/1995 | Vari et al. |
| 5,383,467 A | 1/1995 | Auer et al. |
| 5,384,261 A | 1/1995 | Winkler et al. |
| 5,386,827 A | 2/1995 | Chance et al. |
| 5,398,844 A | 3/1995 | Zaslavsky et al. |
| 5,402,778 A | 4/1995 | Chance |
| 5,402,792 A | 4/1995 | Kimura |
| 5,402,801 A | 4/1995 | Taylor |
| 5,405,369 A | 4/1995 | Selman et al. |
| 5,408,996 A | 4/1995 | Salb |
| 5,408,998 A | 4/1995 | Mersch |
| 5,412,087 A | 5/1995 | McGall et al. |
| 5,413,108 A | 5/1995 | Alfano |
| 5,417,207 A | 5/1995 | Young et al. |
| 5,417,210 A | 5/1995 | Funda et al. |
| 5,419,323 A | 5/1995 | Kittrell et al. |
| 5,421,337 A | 6/1995 | Richards-Kortum et al. |
| 5,421,339 A | 6/1995 | Ramanujam et al. |
| 5,424,180 A | 6/1995 | Saitou |
| 5,424,188 A | 6/1995 | Schneider et al. |
| 5,445,608 A | 8/1995 | Chen et al. |
| 5,445,934 A | 8/1995 | Fodor et al. |
| 5,445,935 A | 8/1995 | Royer |
| 5,449,625 A | 9/1995 | Kobayashi et al. |
| 5,452,723 A | 9/1995 | Wu et al. |
| 5,453,355 A | 9/1995 | Birkenmeyer et al. |
| 5,456,252 A | 10/1995 | Vari et al. |
| 5,457,027 A | 10/1995 | Nadeau et al. |
| 5,461,229 A | 10/1995 | Sauter et al. |
| 5,467,767 A | 11/1995 | Alfano et al. |
| 5,476,774 A | 12/1995 | Wang et al. |
| 5,487,970 A | 1/1996 | Rowley et al. |
| 5,491,063 A | 2/1996 | Fisher et al. |
| 5,492,806 A | 2/1996 | Drmanac et al. |
| 5,494,797 A | 2/1996 | McCann et al. |
| 5,503,979 A | 4/1996 | Kramer et al. |
| 5,506,098 A | 4/1996 | Zarling et al. |
| 5,510,270 A | 4/1996 | Fodor et al. |
| 5,512,757 A | 4/1996 | Cederstrand et al. |
| 5,514,551 A | 5/1996 | Yang et al. |
| 5,517,313 A | 5/1996 | Colvin, Jr. |
| 5,517,997 A | 5/1996 | Fontenot |
| 5,527,681 A | 6/1996 | Holmes |
| 5,538,848 A | 7/1996 | Livak et al. |
| 5,540,691 A | 7/1996 | Elstrom et al. |
| 5,541,062 A | 7/1996 | Smeekens et al. |
| 5,542,928 A | 8/1996 | Evans et al. |
| 5,543,026 A | 8/1996 | Hoff et al. |
| 5,545,523 A | 8/1996 | Batt et al. |
| 5,545,897 A | 8/1996 | Jack |
| 5,547,860 A | 8/1996 | Kocher et al. |
| 5,552,270 A | 9/1996 | Khrapko et al. |
| 5,553,614 A | 9/1996 | Chance |
| 5,555,885 A | 9/1996 | Chance |
| 5,556,421 A | 9/1996 | Prutchi et al. |
| 5,556,749 A | 9/1996 | Mitsuhashi et al. |
| 5,562,100 A | 10/1996 | Kittrell et al. |
| 5,567,586 A | 10/1996 | Croce |
| 5,571,152 A | 11/1996 | Chen et al. |
| 5,571,673 A | 11/1996 | Picone |
| 5,573,907 A | 11/1996 | Carrino et al. |
| 5,573,909 A | 11/1996 | Singer et al. |
| 5,579,773 A | 12/1996 | Vo-Dinh et al. |
| 5,587,472 A | 12/1996 | Dattagupta et al. |
| 5,593,867 A | 1/1997 | Walker et al. |
| 5,596,988 A | 1/1997 | Markle et al. |
| 5,597,692 A | 1/1997 | Coghlan et al. |
| 5,597,911 A | 1/1997 | Guesdon et al. |
| 5,599,668 A | 2/1997 | Stimpson et al. |
| 5,599,675 A | 2/1997 | Brenner |
| 5,599,695 A | 2/1997 | Pease et al. |
| 5,607,834 A | 3/1997 | Bagwell |
| 5,610,012 A | 3/1997 | Luchansky et al. |
| 5,624,711 A | 4/1997 | Sundberg et al. |
| 5,626,139 A | 5/1997 | Szeles et al. |
| 5,629,147 A | 5/1997 | Asgari et al. |
| 5,631,134 A | 5/1997 | Cantor |
| 5,632,740 A | 5/1997 | Koch et al. |
| 5,639,612 A | 6/1997 | Mitsuhashi et al. |
| 5,647,368 A | 7/1997 | Zeng et al. |
| 5,650,278 A | 7/1997 | Barr et al. |
| 5,650,399 A | 7/1997 | Rokita et al. |
| 5,652,099 A | 7/1997 | Conrad |
| 5,653,939 A | 8/1997 | Hollis et al. |
| 5,658,730 A | 8/1997 | McGill et al. |

| | | | | | | |
|---|---|---|---|---|---|---|
| 5,659,025 | A | 8/1997 | Engels et al. | JP | 05-268999 A2 | 10/1993 |
| 5,661,028 | A | 8/1997 | Foote | JP | 06-125797 A2 | 5/1994 |
| 5,667,654 | A | 9/1997 | Gombocz et al. | JP | 06-261795 A2 | 9/1994 |
| 5,667,667 | A | 9/1997 | Southern | JP | 07-88105 A2 | 4/1995 |
| 5,667,974 | A | 9/1997 | Birkenmeyer et al. | JP | 07-289506 A2 | 11/1995 |
| 5,679,512 | A | 10/1997 | Laney et al. | JP | 08-83569 A2 | 3/1996 |
| 5,681,697 | A | 10/1997 | Urdea et al. | JP | 09-95495 A2 | 4/1997 |
| 5,683,881 | A | 11/1997 | Skiena | JP | 09-192138 A2 | 9/1997 |
| 5,690,894 | A | 11/1997 | Pinkel et al. | WO | WO 90/04352 A1 | 5/1990 |
| 5,695,933 | A | 12/1997 | Schalling et al. | WO | WO 90/08838 A1 | 8/1990 |
| 5,696,157 | A | 12/1997 | Wang et al. | WO | WO 90/12536 A1 | 11/1990 |
| 5,700,637 | A | 12/1997 | Southern | WO | WO 90/15595 A1 | 12/1990 |
| 5,707,797 | A | 1/1998 | Windle | WO | WO 91/15151 A1 | 10/1991 |
| 5,707,813 | A | 1/1998 | Dandliker et al. | WO | WO 92/14514 A1 | 9/1992 |
| 5,716,981 | A | 2/1998 | Hunter et al. | WO | WO 92/14845 A1 | 9/1992 |
| 5,730,134 | A | 3/1998 | Dumoulin et al. | WO | WO 92/15253 A1 | 9/1992 |
| 5,769,791 | A | 6/1998 | Benaron et al. | WO | WO 92/15883 A1 | 9/1992 |
| 5,785,658 | A | 7/1998 | Benaron et al. | WO | WO 92/16655 A1 | 10/1992 |
| 5,800,478 | A | 9/1998 | Chen et al. | WO | WO 92/22332 A2 | 12/1992 |
| 5,807,261 | A | 9/1998 | Benaron et al. | WO | WO 93/09668 A1 | 5/1993 |
| 5,829,878 | A | 11/1998 | Weiss et al. | WO | WO 93/18186 A1 | 9/1993 |
| 5,833,603 | A | 11/1998 | Kovacs et al. | WO | WO 93/22678 A2 | 11/1993 |
| 5,849,533 | A * | 12/1998 | Berman et al. ............... 435/69.3 | WO | WO 93/22680 A1 | 11/1993 |
| 5,861,253 | A | 1/1999 | Asgari et al. | WO | WO 94/11530 A1 | 5/1994 |
| 5,885,293 | A | 3/1999 | McDevitt | WO | WO 94/13191 A1 | 6/1994 |
| 5,928,137 | A | 7/1999 | Green | WO | WO 95/03428 A1 | 2/1995 |
| 5,928,222 | A * | 7/1999 | Kleinerman ................... 606/16 | WO | WO 95/05391 A1 | 2/1995 |
| 5,935,119 | A | 8/1999 | Guy et al. | WO | WO 95/06062 A1 | 3/1995 |
| 5,984,861 | A | 11/1999 | Crowley | WO | WO 95/11262 A1 | 4/1995 |
| 6,008,014 | A | 12/1999 | Gimeno et al. | WO | WO 95/11995 A1 | 5/1995 |
| 6,119,031 | A | 9/2000 | Crowley | WO | WO 95/12349 A1 | 5/1995 |
| 6,122,536 | A | 9/2000 | Sun et al. | WO | WO 95/25538 A1 | 9/1995 |
| 6,185,443 | B1 | 2/2001 | Crowley | WO | WO 95/28169 A1 | 10/1995 |
| 6,201,989 | B1 | 3/2001 | Whitehead et al. | WO | WO 96/05693 A1 | 2/1996 |
| 6,219,137 | B1 | 4/2001 | Vo-Dinh | WO | WO 96/06946 A1 | 3/1996 |
| 6,238,348 | B1 | 5/2001 | Crowley et al. | WO | WO 96/07451 A2 | 3/1996 |
| 6,289,229 | B1 | 9/2001 | Crowley | WO | WO 96/17933 A2 | 3/1996 |
| 6,322,495 | B1 | 11/2001 | Snow et al. | WO | WO 96/24406 A1 | 8/1996 |
| 6,324,418 | B1 | 11/2001 | Crowley et al. | WO | WO 96/27664 A2 | 9/1996 |
| 6,343,227 | B1 | 1/2002 | Crowley | WO | WO 96/31622 A1 | 10/1996 |
| 6,364,831 | B1 | 4/2002 | Crowley | WO | WO 96/36737 A1 | 11/1996 |
| 6,405,073 | B1 | 6/2002 | Crowley et al. | WO | WO 96/39932 A1 | 12/1996 |
| 2001/0041862 | A1 * | 11/2001 | Glickman ................ 604/101.01 | WO | WO 97/01985 A1 | 1/1997 |
| | | | | WO | WO 97/10365 A1 | 3/1997 |

FOREIGN PATENT DOCUMENTS

| | | |
|---|---|---|
| DE | 888727 | 9/1953 |
| DE | 3023130 A1 | 1/1982 |
| DE | 4005743 A1 | 2/1990 |
| DE | 4119075 A1 | 12/1992 |
| DE | 4213703 A1 | 10/1993 |
| DE | 19512518 A1 | 10/1995 |
| DE | 19617940 A1 | 10/1997 |
| EP | 0304321 A1 | 2/1989 |
| EP | 0314937 A2 | 5/1989 |
| EP | 0326395 A2 | 8/1989 |
| EP | 0333561 B1 | 9/1989 |
| EP | 0382433 B1 | 8/1990 |
| EP | 0439968 A1 | 8/1991 |
| EP | 0531027 A1 | 3/1993 |
| EP | 0578138 A2 | 1/1994 |
| EP | 0582256 A2 | 2/1994 |
| EP | 0629380 A1 | 12/1994 |
| EP | 0639647 A2 | 2/1995 |
| EP | 0650694 A1 | 5/1995 |
| EP | 0721016 A2 | 7/1996 |
| EP | 0728440 B1 | 8/1996 |
| EP | 0742287 A2 | 11/1996 |
| EP | 0777119 A2 | 6/1997 |
| EP | 0785280 A2 | 7/1997 |
| EP | 0792618 A1 | 9/1997 |
| EP | 0794261 A2 | 9/1997 |
| EP | 0799897 A1 | 10/1997 |
| EP | 0801132 A2 | 10/1997 |
| EP | 0808899 A2 | 11/1997 |
| EP | 0920831 A1 | 6/1999 |
| JP | 63-246393 A | 10/1988 |
| JP | 02-75958 A2 | 3/1990 |
| JP | 02-223828 A2 | 9/1990 |
| JP | 05-103700 A2 | 4/1993 |

| | | |
|---|---|---|
| WO | WO 97/14816 A1 | 4/1997 |
| WO | WO 97/22720 A1 | 6/1997 |
| WO | WO 97/27317 A1 | 7/1997 |
| WO | WO 97/27325 A2 | 7/1997 |
| WO | WO 97/29210 A2 | 8/1997 |
| WO | WO 97/29212 A1 | 8/1997 |
| WO | WO 97/31256 A2 | 8/1997 |
| WO | WO 97/35869 A1 | 10/1997 |
| WO | WO 97/39008 A1 | 10/1997 |
| WO | WO 97/42417 A1 | 11/1997 |
| WO | WO 97/43450 A1 | 11/1997 |
| WO | WO 98/22805 A1 | 5/1998 |

OTHER PUBLICATIONS

Bollinger, et al., "LESIT Project 4.04—Intergrated UV Sensor," Internet publication, 1995.

Coleman, et al., "Acoustic Emission and Sonoluminescence Due to Caviitation at the Beam Focus of an Electrohydraulic Shock Wave Lithotripter," *Ultrasound in Medicine and Biology* 18(3):267, 281 (1992).

Cothren, et al., "Gastrointestinal Tissue Diagnosis by Laser-Induced Fluorescence Spectroscopy at Endoscopy," *Gastrointestinal Endoscopy* 36(2):105-111 (1990).

Crowley, et al., "Ultrasound Guided Therapeutic Catheters: Recent Developments and Clinical Results," *International Journal of Cardiac Imaging* 6:145-156 (1991).

Huang et al., "Fluorescence Diagnosis of Gynecological Cancerous and Normal Tissues," *Proceedings of SPIE (International Society for Optical Engineering)* 2134:42-45 (1994).

Kapadia, et al., "Laser-Induced Fluorescence Spectroscopy of Human Colonic Muscosa," *Gastroenterology* 99(1):150-157 (1990).

Ko, "Biomedical Sensors and Actuators," *Electronics in Medicine and Biology* 26-53-26-68 (1989).

Kopp, et al., "Stay Tuned: Photonic Filters Color Your World," *Photonics Spectra* 125-129 (1997).

Lilge, et al., "Light Induced Fluorescence Spectroscopy at Endoscopy," presented at the 10th Asian Pacific Congress on Gastroenterology.

Meindl, "Implantable Telemetry in Biomedical Research," *Electronics in Medicine and Biology* 26-41-26-52 (1989).

Petrofsky, "In Vivo Measurement of Brain Blood Flow in the Cat," *IEEE Transactions on Biomedical Engineeering* 26(8):441-445 (Aug. 1979).

Vona, et al., "A Test of the Hypothesis That Cavitation at the Focal Area of an Extracorporeal Shock Wave Lithotripter Produces Far Ultraviolet and Soft X-ray Emissions," *Journal of the Acoustical Society of America* 98(2):706-710 (August).

International Search Report, PCT/US97/20324 (Mar. 11, 1998).
International Search Report, PCT/US97/20367 (Mar. 23, 1998).
International Search Report, PCT/US97/20435 (May 19, 1998).
International Search Report, PCT/US98/20019 (Jan. 20, 1999).
International Search Report, PCT/US98/20018 (Jan. 21, 1999).
International Search Report, PCT/US98/21100 (Feb. 8, 1999).

* cited by examiner

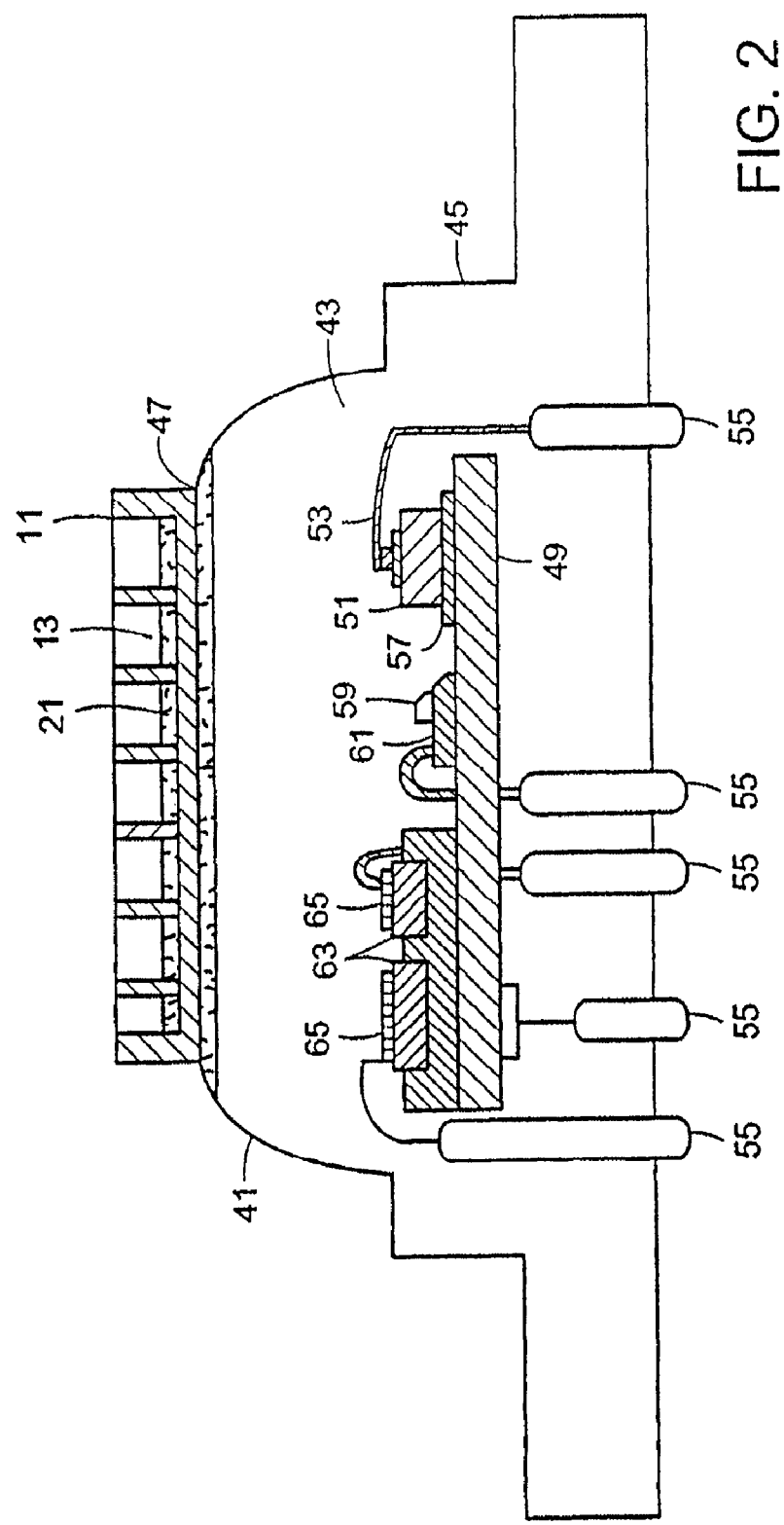

READABLE PROBE ARRAY FOR IN VIVO USE

CROSS-REFERENCES TO RELATED APPLICATIONS

This application is a continuation of U.S. application Ser. No. 09/881,283, filed Jun. 14, 2001, now U.S. Pat. No. 7,302,289, which is a continuation of U.S. application Ser. No. 09/233,409, filed Jan. 19, 1999, now U.S. Pat. No. 6,289,229, which claims the benefit of U.S. Provisional Application No. 60/071,906, filed Jan. 20, 1998. The entire disclosures of the above applications are incorporated herein by reference.

BACKGROUND

Polydeoxynucleotide and oligonucleotide sequencing with laboratory-based instruments has become inexpensive and reliable due to the variety and availability of complimentary fluorescent labeled target sequences. These fluorescent labeled probes may be specially tailored to hybridize with genomic DNA segments and form base pair matches that can accurately detect the presence of inherited genetic disorders or native-cell mutations. Under excitation light in the visible or UV range, the associated fluorescent marker attached to the probe emits a secondary emission that may be detected by a charge-coupled device (CCD) array, photodiode, or other spectrally sensitive light detector.

However, current techniques require the use of specialized reagents and additional processing to separate the cell wall and other components before analysis. The analyte is removed and introduced into an assay chamber for analysis. The chambers are housed in portable or tabletop analytic instruments that typically contain an excitation source, detection sensors, spatial reading or imaging devices, and archiving capabilities. These systems are expensive and require that tissue samples be processed prior to use. The biggest drawback to these types of systems is their inherent inability to perform fast, localized reading of array probes in a convenient and repeatable manner in vivo. In vivo monitoring and detection of changes to the human body in response to therapy is needed to expedite trials and to monitor results from therapy, and would allow doctors to treat serious diseases such as cancer safely in a more effective and less costly manner.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present invention performs specific detection and analysis of biological analytes in vivo using a simplified, low-cost set of components. In one embodiment, the small size and simplified operation allow the entire device to be housed in a catheter. In one aspect, the device consists of a housing, a light excitation source, a detector, and at least one fluorescent-labeled probe material on a substrate that is exposed to the tissue of the body. The excitation source may be directed at the substrate carrying the probe, or may be a conductor of the excitation energy. Other embodiments include the use of a lumen to introduce a lysing agent or energy to the area of interest. The lysing agent or energy may be an ultrasonic transducer capable of rupturing cell membranes through the use of a brief burst of ultrasonic energy. In another aspect, a lysing system is used in which pressurization and evacuation of the sample via the lumen adjacent to the probe array creates a pressure capable of rupturing the cell membrane. Each of the probes may be read by application of electrical current to the excitation source and by detecting the presence or absence of signal via the probe sensor. The probe sensor may be a photodiode that is responsive to light emitted by the fluorescent probe material. Two probes may be mixed and read by two sensors if the spectrum is sufficiently separated. A ratio can then be obtained to facilitate analysis. In another embodiment, a normalizing patch may be adjacent to provide a reference signal, thereby simplifying the calibration of the instrument.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 2 is a cross-sectional view of a readable polydeoxynucleotide array module and system.

DETAILED DESCRIPTION

Figure 1:
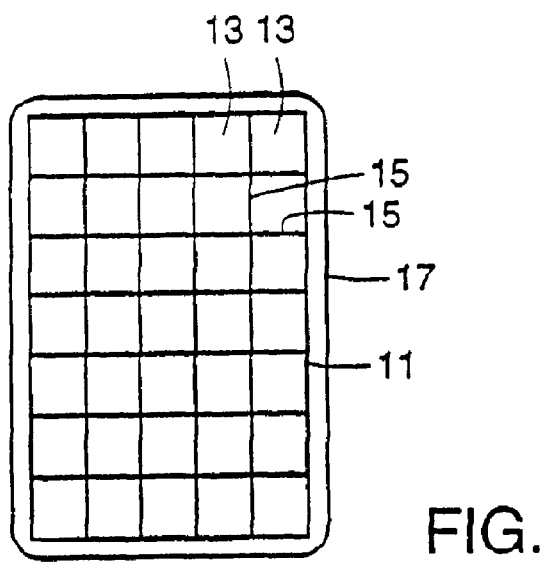
FIG. 1 is a planar view of a probe array containing a multiplicity of fluorescent probes on its surface.

Referring now to FIG. 1, the planar view of a probe array 11 is shown as a grid-like array with a plurality of chambers 13 arranged to have separators 15 within a frame 17. The frame 17 may be a small injection-molded component made of a plastic, such as polystyrene, or a molded material, such as glass. The separators 15 may be molded integrally to the frame 17 or may be separate elements placed within it. The overall dimensions of the frame 17 may be small. Typical dimensions are less than 1 mm by 1 mm.

Figure 1A:
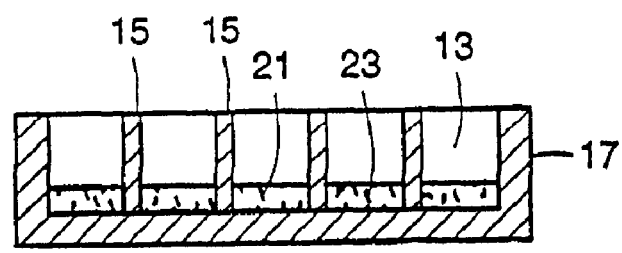
FIG. 1A is a cross-sectional view of the probe array of FIG. 1.

Referring now to FIG. 1A, which is a cross-sectional view of the probe array 11, the aforementioned separators 15 are effective to separate a fluorescent probe material 21 that may have different characteristics from an adjacent fluorescent probe material 23. Probe materials 21 and 23 are generally deposited in a thin layer on top of a substrate, in this case, the material of the frame 17. Alternatively, the frame 17 may be made of a foraminous material or a partly foraminous substance such as sol gel (not shown). The probe materials may be incorporated into the substrate, which may be a flat surface that allows ink printing processes to be used to deposit the probe array materials at high speeds and at low cost.

Probe materials generally are engineered molecular materials that are designed to have an affinity to one or more constituents that may be expected to be found in the tissue, fluid, or chemical mix to be analyzed. These probe materials may be made sensitive to specific genes or gene segments through complimentary genetic indicators that have been designed to fluoresce or change color, as observed by the naked eye or by spectrographic analysis methods, when they are linked to a molecule to which they have affinity. A large number of different types and combinations of optically readable probes are being manufactured today that have specific affinity to one or more genes, proteins, or other chemicals. In preferred embodiments, the present invention contemplates the use of two classes of probes: (i) protein sensitive probes, such as GFP (green fluorescent probe) from the jellyfish *Aequorea Victoria*; and (ii) modified oligonucleotide probes that are fluorogenic, such as those manufactured by Synthegen LLC, Houston, Tex. 77042. Additional probes suited for use in the present invention are available from Midland Certified Reagent Company, Midland, Tex. 79701, and Transbio Corp., Baltimore, Md. 21220. Typically, these probes must be used in vitro due to either their lack of biocompatibility or because they must be used in conjunction with aggressive reagents that are toxic to cells.

Figure 1B:
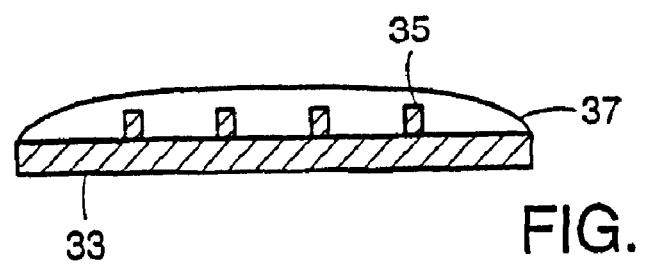
FIG. 1B is a cross-sectional view of a sheet of material carrying a probe array.

Various methods and configurations may be used to deposit or arrange probe locations and positions in an array or singly. For instance, a sheet of plastic material 33, as shown in FIG. 1B, may have lines 35 made of probe-filled ink printed in any arrangement that may be produced with printing methods. More than one type of probe-filled ink may be used to produce various patterns and arrangements, including overlapping patterns (not shown). The ink pattern lines 35 may be protected with a topcoat 37 that may be made of a dissolvable gel such as ordinary gelatin, or another material such as soluble or even a waterproof polymer that only dissolves and provides access to the probe material in the probe-filled ink in lines 35 after the application of a solvent. The arrangement of the sensitive areas by this process allows the probe materials to be applied to a variety of surfaces and substrates, including medical devices, such as needles, trocars, forceps, catheters, guidewires, implants, and prostheses, in an inexpensive and reliable manner.

The following discussion and description of the present invention is directed to a readable polydeoxynucleotide array module (RPAM). However, those skilled in the art will appreciate that the present invention and specific embodiments described below may be utilized with any number of probe arrays and the RPAM described here is provided as only one non-limiting example.

Referring now to FIG. 2, which is a cross-sectional view of a readable polydeoxynucleotide array module (RPAM) 41, the probe array 11 may be positioned adjacent to a spectrometer module that is encapsulated in an at least partly transparent housing 45. The probe array 11 may be cemented to the side, top, or other area within a spectrometer module 43 with an optical cement (not shown), or by a solvent bond line 47 that allows two plastics to be fused through partial melting. A spectrometer module suitable for use in this invention has been described in pending U.S. patent application Ser. No. 08/898,604, the entire disclosure of which is incorporated by reference herein.

Specifically, the spectrometer module used in the present invention includes a light source and a light detector for placement inside a body such that optical conduits are not necessary to deliver light signals to and from the RPAM inside the body. The miniature spectrometer includes the light source and one or more light detectors. The light source illuminates a tissue region and the light detectors detect optical properties of the illuminated tissue by measuring modified light signals. The light detectors convert optical signals to electrical signals such that one or more electrical wires placed inside an interventional device can deliver the electrical signals from the RPAM to a signal display or a microprocessor.

The light source and the light detectors are energized by an external power supply through electrical wires. In another embodiment, an optically transparent tip encapsulates a spectrometer. The tip is shaped to optimize tissue contact and optical transmission. The tip encapsulating the spectrometer is disposed at a distal end of an interventional device. The tip may be coated with a material to improve light transmission. The tip may include at least one fluid channel, which is in communication with a lumen inside the interventional device, to deliver a fluid to a tissue region. The spectrometer may also include a light source and the light detectors formed on a single substrate. The light source may be a light-emitting diode and the light detectors may be a photodiode comprising multiple channels, where both devices are formed on a silicon substrate. The light detector can include multiple channels to detect light emission at multiple wavelengths.

Still referring to FIG. 2, probe array 11 may be integrally molded onto the surface of the spectrometer module 43, creating a somewhat simplified one-piece unit that may provide processing advantages in high-speed production environments where parts counts are intentionally kept low to minimize stock and therefore reduce cost of fabrication and assembly. Injection molding or casting of the components is effective to produce miniature components that correspond in size to conventional silicon-based integrated circuit scale. Therefore, it should be appreciated that the RPAM may be small, e.g., about the size of a miniature electronic component such as a surface mount device. Such devices include packaging, leads, and other components, and may be obtainable in size ranges of less than 1 mm in length. Such devices may typically be configured in the range from about 0.5 mm to about 3 mm to produce small, useful devices for in vivo use. The RPAM 41 may also have printable surfaces according to the construction of alternative probe array configurations as described in FIG. 1A and FIG. 1B, if desired. Referring once again to FIG. 2, the internal components of the RPAM consist of a substrate material 49 such as silicon upon which a light-emitting diode light source 51 is mounted with power lead 53 attached to one of terminals 55. Various colors and types of diode light sources may be used, including those now available that emit light in the infrared, the red, the yellow, the green, the blue, and the blue-violet regions. A working range of RPAM excitation wavelengths is from about 1100 nanometers to about 250 nanometers and may comprise monochromatic, bichromatic, or broadband emissions. The exit aperture 57 is positioned to illuminate a movable mirror 59 that is bonded to piezoelectric stack actuator 61. Empowerment of the stack actuator 61 is effective to direct light emission from diode light source 51 to one or more chambers 13. Light emission from the probe materials 21 is picked up by one or more light detectors 63 through filters 65. Signals from the detectors 63 are brought out from the RPAM through other terminals 55.

Figure 2A:
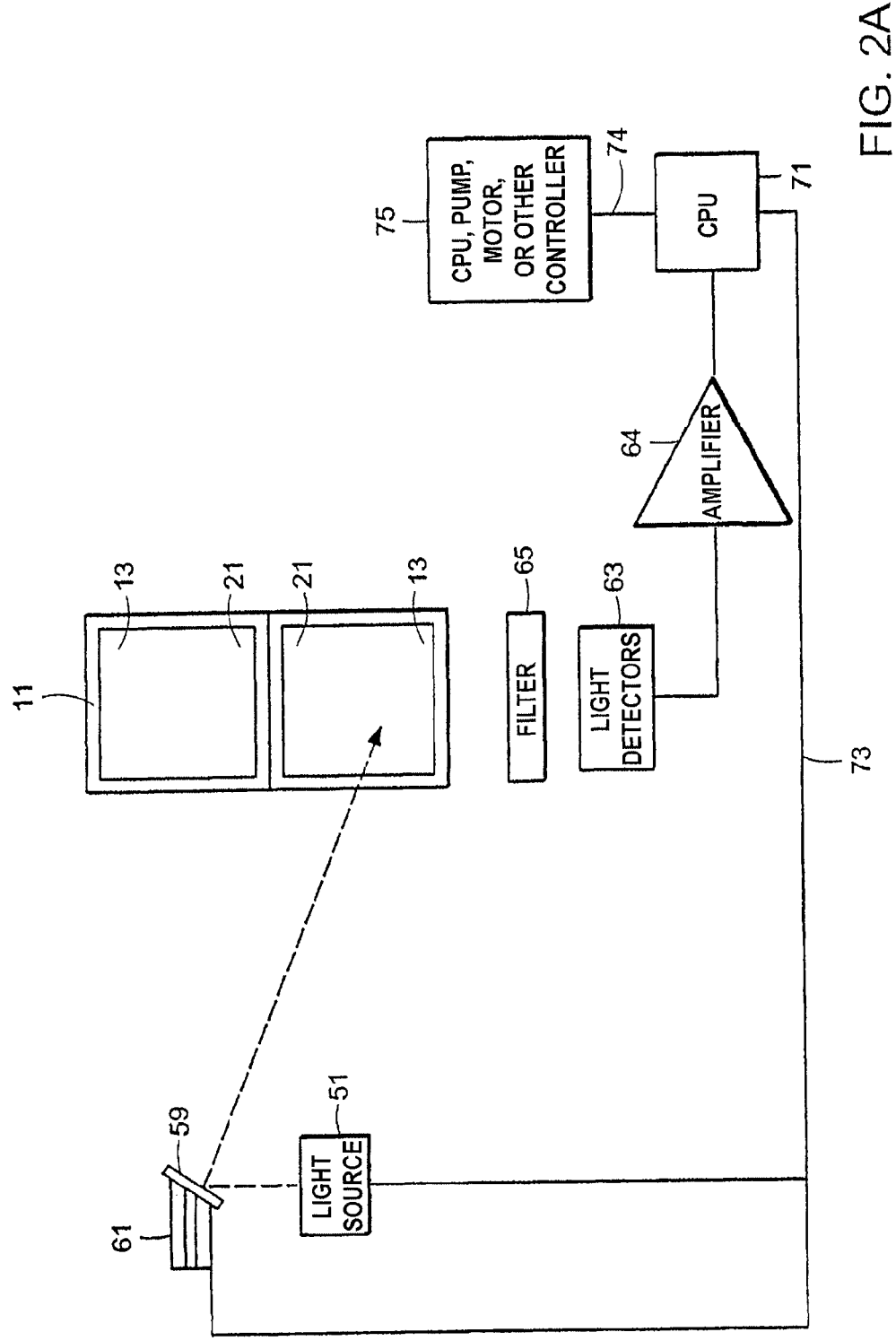
FIG. 2A is a block diagram of the readable polydeoxynucleotide array module and system.

Referring now to FIG. 2A, the operation of the RPAM is depicted in block diagram form as follows: Light is generated and directed from light source 51 and directed at one or more of chambers 13 by mirror 59, which impinges upon at least one probe material 21. Fluorescence or other secondary light generated by the action of the light energy upon the probe material causes a second emission that may be detected by one or more light detectors 63 after passing through a band-pass filter 65. The signal may be amplified and/or conditioned by one or more amplifier stages 64. Filters 65 allow the system to discriminate between various secondary light emission wavelengths, and signals from said light detectors 63 may be synchronized with the operation of light source 51 so that at any given time there is a known relationship between the particular probe that is illuminated and its response as detected by the light detectors. The timing and relationship of the light-generating, light-detecting event and the spatial position of the mirror 59 are controlled by CPU 71 and sent to the components via control lines 73.

The data obtained may be stored or presented in a display device or other therapeutic device that can be a graphical display, a television monitor, printout or drug delivery pump, interventional device, motor or actuator, etc. Accordingly, this apparatus may effectively scan or read a plurality of probe materials in a repeatable, fast, and controllable manner; and the information read may be stored, displayed, or used to initiate another action such as a therapeutic application of a drug, or control of a motor. The bandpass filter system of detecting one or more light wavelengths for this purpose is basic, and more complex schemes could be employed by those of ordinary skill in the art. Such schemes may include, without limitation, light wavelength detection systems comprising gratings, graduated filters, heterodyne detection, acousto-optic tunable filtering, and other light detectors that effectively provide an amplitude and frequency responsive signal. A diffraction grating (not shown), for instance, may be attached to movable mirror 59 to provide spatial and chromatic control simultaneously.

Figure 3:
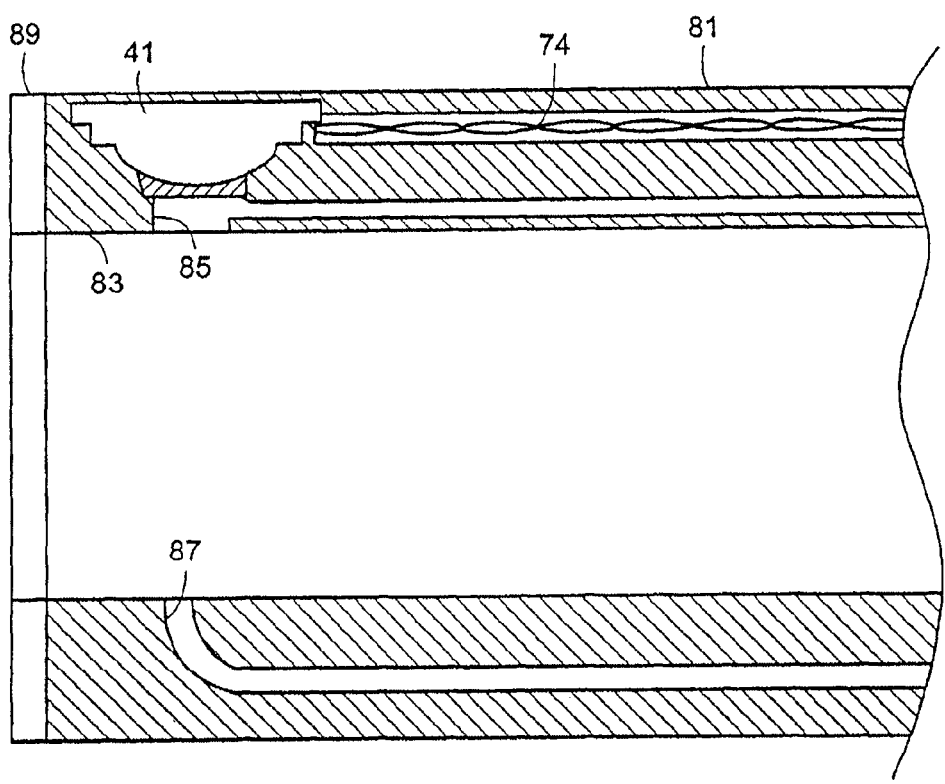
FIG. 3 is a cross-sectional view of an interventional device carrying the readable polydeoxynucleotide array module.

FIG. 3 is the cross-sectional view of an interventional device incorporating the spectrometer and probe still referred to here as RPAM 41; there is a body-insertable appliance 81 such as a catheter that may have a distal end and a proximal end and may consist of a plastic, rubber, or metal material that is generally elongated in shape, has a small cross section allowing it to pass easily through the body, and has one or more lumens or conduits that may extend through the length of the device. Shown in FIG. 3 is a device having three lumens, although a greater or lesser number of lumens may be used, depending upon the application for which the device is intended. The main lumen 83 is relatively large and is used to deliver a drug, a reagent, or a device to or beyond the distal tip 89. Suction lumen 85 is useful for drawing biological fluids, tissue, or other materials into proximity with the RPAM 41, where the material can be analyzed. Signal wires 74 may extend to an external controller (not shown) or to a CPU, pump, motor, or other controller as shown in FIG. 2A, 75.

Returning once again to FIG. 3, infusion lumen 87 may provide additional fluids, reagents, drugs, wires, or appliances that may be useful to the procedure. For example, the practitioner will appreciate that additional reagents can be introduced to facilitate analysis. Such additional reagents can include: denaturants, such as guanidinium thiosulfate; buffers, such as Tris-Cl; detergents, such as SDS; chelators, such as EDTA; enzymes, such as proteinases and/or DNAases; and other reagents known to those of ordinary skill in the art that may be appropriate to the particular analysis to be carried out using the apparatus of the present invention.

Figure 4:
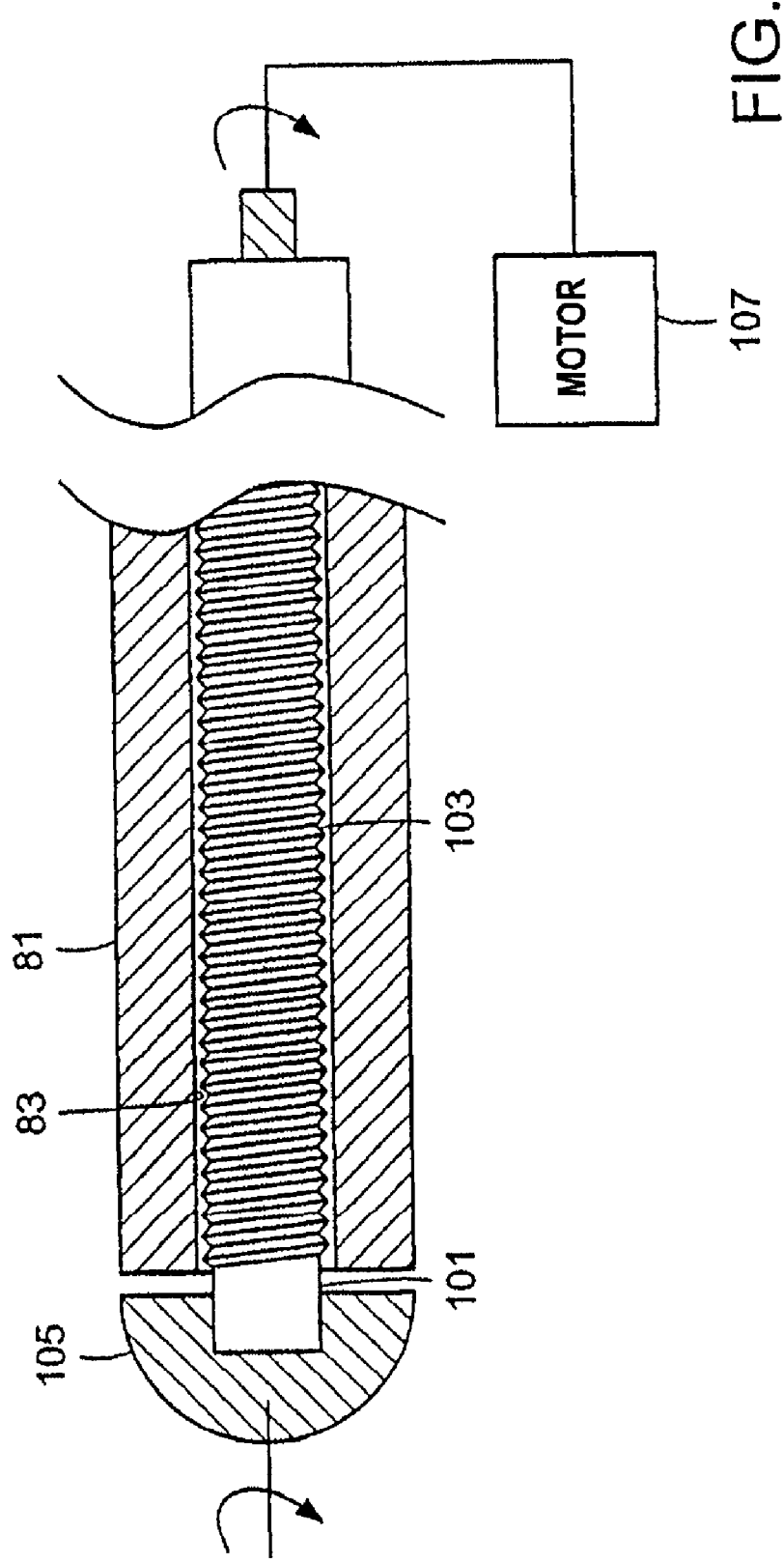
FIG. 4 is a cross-sectional view of an interventional device fitted with a lysing core.
Figure 5:
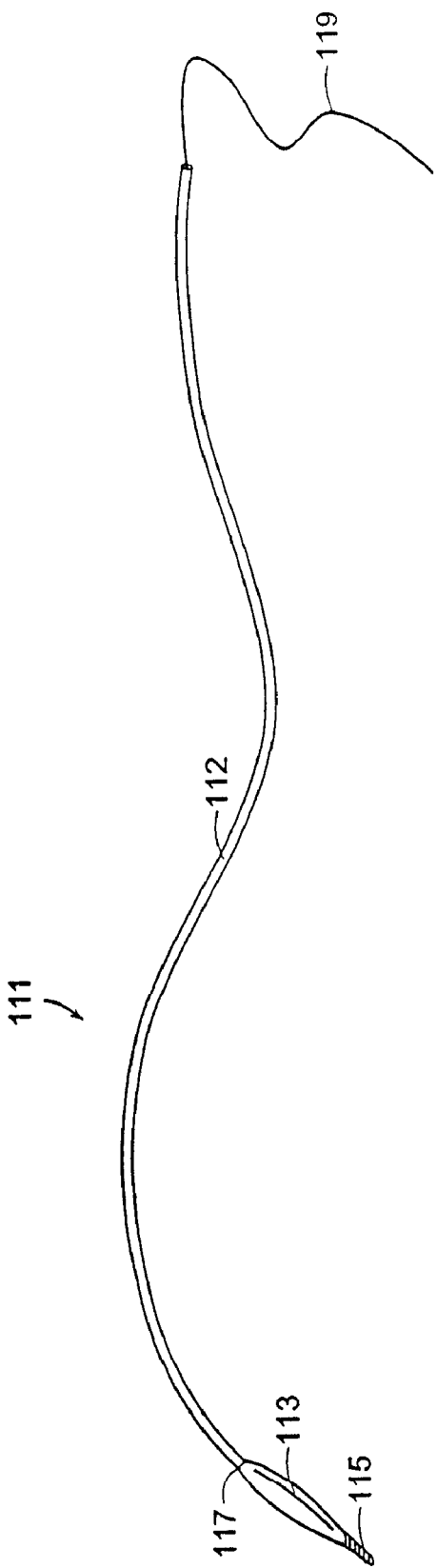
FIG. 5 is a side view of a secondary insertable device having a tip and a multifilar shaft.

Referring now to FIG. 4, a cross-sectional view of an interventional device, such as a body-insertable appliance 81 fitted with a lysing core 101, is shown. The lysing core 101 utilizes mechanical motion to disrupt cells in order to make the cell contents available for analysis by the RPAM (not shown). The use of a lysing device in conjunction with the RPAM system eliminates the need for potentially toxic reagents that are commonly used to open cells in vitro. The lysing head 105 consists here of a more or less hemispherical component that may be comprised of a metal or plastic, which is mounted at the distal end of a driveshaft 103. Such driveshafts are well known for their ability to deliver torque and rotary motion from a proximal motor 107 or by hand control. As taught in this invention, motor 107 is one of a class of components shown in FIG. 2A as 75 which may be controlled by system CPU 71, also shown in FIG. 2A. Numerous other lysing devices are known that may abrade, disrupt, dissolve, pressurize, vacuum, cavitate, or otherwise apply mechanical forces to a cell or cells that are effective to disrupt the cell and make its contents available for analysis. It should be pointed out that such damage to cells is usually minimized to avoid permanent damage to the organ, vessel, duct, or tissue being tested. The lysing head 105 need not be relatively large and may be made small enough so that it may easily pass through the device from the proximal end so that another device or implant may be inserted, if needed, through the same large lumen 83. Such an implant may be a solid or porous, foraminous, or dissolvable seed, implant, stent, gel, or the like, which may carry therapeutic agents to a particular site in the body. This system provides the advantage that local conditions can be determined through use of the polydeoxynucleotide-readable array (afforded by the construction of the RPAM device as described herein); and, therefore, better and more precise application of appropriate medicaments, drugs, therapeutic genetically based substances, etc., is facilitated. Further advantages are provided in that the information is obtained at or near real time, and that information is obtainable from the exact location of a proposed therapeutic intervention. Such a device that may be used to place an implant is shown in FIG. 5, which is a side view of a secondary insertable device 111 comprising a rotary, multifilar, flexible driveshaft 112 having a therapeutic tip 113 terminating in an anchoring device 115 shown as a screw form capable of being screwed into tissue until separable joint 117 breaks, after which the remaining part of insertable device 111 may be withdrawn. Driveshaft 112 may be hollow, to allow tether 119 to remain attached to therapeutic tip 113. Tether material may be constructed of a wire to allow the sending and receiving of an electrical signal, or may simply be used as a retrieval device to retrieve any portion of the therapeutic tip that may remain after the need for it is over.

Figure 6:
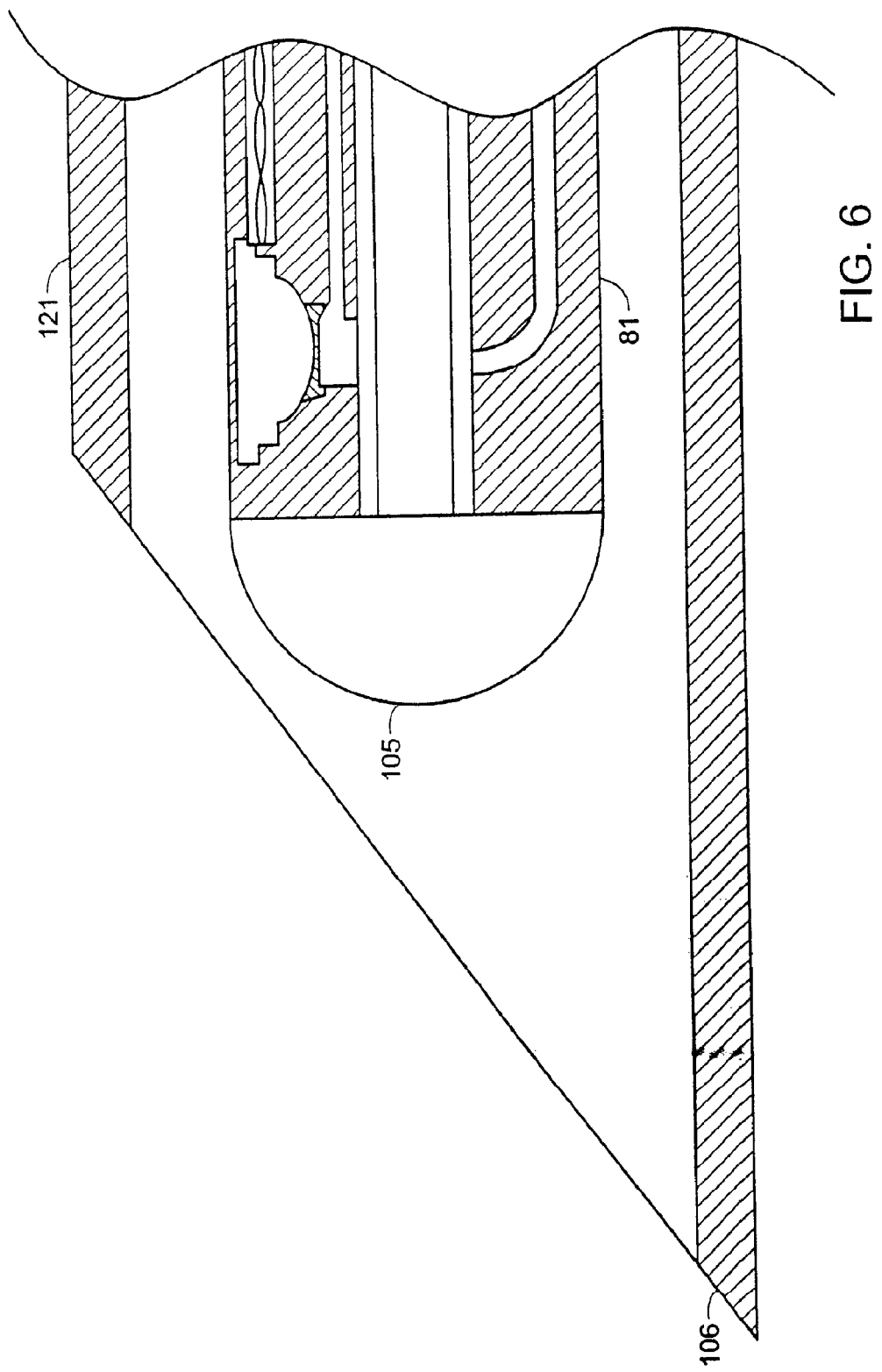
FIG. 6 is a cross-sectional view of a hollow needle carrying the readable polydeoxynucleotide array module equipped insertable appliance.

Numerous carrying devices may be used to deliver the RPAM. FIG. 6 is a cross-sectional view of a hollow needle 121 carrying the RPAM insertable appliance 81. The advantage of a needle is that it allows the introduction of the RPAM into portions of the body where there is no natural passageway. This method allows the user to position the distal tip of the lysing head 105 in various positions with respect to the sharp needle tip 106. The needle may be of stainless steel and may be inserted into body tissue such as muscle, breast, prostate, or cardiac tissue. The needle may be left in place, and the RPAM withdrawn temporarily to allow another appliance (not shown) to be introduced. Other carrying devices may include guidewires, balloon catheters, ultrasound catheters with both imaging or non-imaging, and rotatable or array configurations, introducer sheaths, balloon angioplasty catheters for use in the blood vessels of the heart, the extremities, and the vascular system, atherectomy catheters, and many other types of interventional devices, as well as intraoperative devices. The device of the invention may be used anywhere there is the need for fast, precise localized detection and analysis of nucleotides, proteins, or the like, either for diagnostic purposes, or to guide therapy which itself may be made more localized, and therefore site-specific. Such uses are economical and have less impact on surrounding tissue that is free of disease. The invention allows use of any agent that may change color as a result of the application of a local chemical to be read and includes, without limitation, such agents as litmus, photodynamic therapeutic agents, such as photofrin, fluorescent agents or dyes, staining dyes, luciferin, etc. The present invention permits analysis in a real time fashion without the need to remove and transport tissue specimens for later analysis.

While illustrative embodiments have been illustrated and described, it will be appreciated that various changes can be made therein without departing from the spirit and scope of the invention.

The embodiments of the invention in which an exclusive property or privilege is claimed are defined as follows:

1. A body-insertable apparatus comprising:
   an excitation source capable of generating radiation;
   at least one probe disposed in a path of said radiation, said probe having an affinity to an analyte and situated in the apparatus to contact the analyte and receive the generated radiation at a same time;
   a detector for detecting the optical properties of said probe, said detector also for converting optical signals representative of the detected optical properties to electrical signals; and
   a housing adapted for reaching an area of interest within a body,
   wherein said excitation source, said probe, and said detector are disposed in said housing.

2. The apparatus of claim 1 wherein said probe binds to at least one of an oligonucleotide and a protein.

3. The apparatus of claim 1 wherein said probe is fluorescently labeled.

4. The apparatus of claim 1 wherein said probe is attached to a substrate.

5. The apparatus of claim 1 wherein said probe comprises an array of sub-probes.

6. The apparatus of claim 5 wherein said array comprises a readable polydeoxynucleotide array.

7. The apparatus of claim 6 wherein said array is positioned adjacent to said detector.

8. The apparatus of claim 7 wherein said detector comprises a spectrometer module.

9. The apparatus of claim 8 wherein said spectrometer module is encapsulated in an at least partly transparent housing.

10. The apparatus of claim 5 wherein said array is disposed in a plurality of chambers within a frame.

11. The apparatus of claim 10 wherein said frame comprises at least one of a molded material and a foraminous material.

12. The apparatus of claim 1, further comprising optics that affect said path of radiation.

13. The apparatus of claim 12 wherein said optics comprise a mirror.

14. The apparatus of claim 13 wherein said mirror is adjustable.

15. The apparatus of claim 1 wherein said body-insertable apparatus is electrically connected to a processing unit.

16. The apparatus of claim 1 wherein said body-insertable apparatus is electrically connected to an amplifier.

17. The apparatus of claim 1 wherein said body-insertable apparatus is electrically connected to a display.

18. The apparatus of claim 1 wherein said excitation source comprises a light-emitting diode light source.

19. The apparatus of claim 1 wherein said excitation source provides excitation energy wavelengths in a range from about 1100 nm to about 250 nm.

20. The apparatus of claim 1 wherein said detector comprises a photodiode responsive to light emitted by said probe.

21. The apparatus of claim 1 wherein said detector comprises a light wavelength detection system.

22. The apparatus of claim 21 wherein said light wavelength detection system comprises a bandpass filter.

23. The apparatus of claim 1, further comprising a catheter, wherein said housing is disposed within the catheter.

24. The apparatus of claim 23 wherein said catheter defines one or more lumens extending through the length of the catheter.

25. The apparatus of claim 24 comprising means for delivering a drug, a reagent or a device.

26. The apparatus of claim 24 comprising means for providing suction sufficient to draw an analyte into proximity with said excitation source, said probe and said detector such that said analyte can be analyzed.

27. The apparatus of claim 24 comprising means for infusing fluids, reagents, drugs, wires or appliances.

28. The apparatus of claim 1 wherein said detector comprises multiple channels to detect light emission at multiple wavelengths.

29. The apparatus of claim 1, wherein said probe has readable optical properties when said analyte is in contact with said probe.

30. The apparatus of claim 1, wherein said probe includes a material sensitive to a gene or gene segment.

31. The apparatus of claim 1, wherein said probe is capable of linking to the analyte.

32. A method of performing in vivo examination of a mammalian body, said method comprising:
   (a) providing a device comprising an excitation source, at least one probe having an affinity to an analyte, a detector, and a housing wherein said excitation source, said probe and said detector are disposed in said housing;
   (b) inserting said device into said mammalian body until said probe contacts an analyte in an area of interest;
   (c) generating radiation from said excitation source such that said probe is in a path of said radiation;
   (d) detecting an optical signal representative of an optical property of said probe through said detector, when said analyte is in contact with said probe; and
   (e) converting said optical signal to an electrical signal.

33. The method of claim 32, further comprising contacting said probe with an analyte comprising at least one of an oligonucleotide and a protein.

34. The method of claim 32, further comprising contacting said analyte with a fluorescently labeled probe.

35. The method of claim 32, further comprising attaching said probe to a substrate.

36. The method of claim 35, further comprising mixing said probe with an ink to form a probe-filled ink and depositing said probe-filled ink upon said substrate.

37. The method of claim 36, further comprising depositing a plurality of probe-filled inks upon said substrate in a specific ink pattern.

38. The method of claim 37, further comprising protecting said ink pattern with a topcoat.

39. The method of claim 38, further comprising providing said topcoat made of a dissolvable gel.

40. The method of claim 38, further comprising providing said topcoat made of a polymer material dissolvable only upon application of a solvent.

41. The method of claim 32, further comprising providing said probe with an array of sub-probes.

42. The method of claim 41, further comprising providing said array with a readable polydeoxynucleotide array.

43. The method of claim 41, further comprising providing said array in a plurality of chambers within a frame.

44. The method of claim 43, further comprising providing said frame made of at least one of a molded material and a foraminous material.

45. The method of claim 32, further comprising using optics to affect said path of radiation.

46. The method of claim 45 wherein said step of using optics comprises adjusting a mirror.

47. The method of claim 32, further comprising transmitting and processing said electrical signal.

48. The method of claim 32, further comprising amplifying said electrical signal.

49. The method of claim 32, further comprising displaying said electrical signal.

50. The method of claim 32, further comprising providing a detector comprising a spectrometer module.

51. The method of claim 50, further comprising encapsulating said spectrometer module in an at least partly transparent housing.

52. The method of claim 32, further comprising providing an excitation source that comprises a light-emitting diode.

53. The method of claim 32 wherein step (c) comprises generating radiation of wavelengths in a range from about 1100 nm to about 250 nm.

54. The method of claim 32, further comprising providing said detector comprising a photodiode responsive to said optical signal from said probe.

55. The method of claim 32, further comprising providing said detector comprising a light wavelength detection system.

56. The method of claim 55, further comprising providing said light wavelength detection system comprising a band-pass filter.

57. The method of claim 32, further comprising providing a catheter comprising said device.

58. The method of claim 32, further comprising providing a catheter having at least one lumen extending through the length of said catheter.

59. The method of claim 58, further comprising delivering a drug, a reagent, or a device through said lumen to or beyond a distal tip of said device to affect said area of interest.

60. The method of claim 58, further comprising using said lumen to provide suction such that said analyte is drawn into contact with said probe.

61. The method of claim 32, further comprising implanting said device in said mammalian body.

62. The method of claim 32, further comprising using a carrying device to deliver said device to the area of interest.

63. The method of claim 62, further comprising providing said carrying device selected from the group consisting of a hollow needle, a guidewire, a balloon catheter, an ultrasound catheter, an introducer sheath, and a balloon angioplasty catheter.

64. The method of claim 32, wherein said probe includes a material sensitive to a gene or gene segment.

65. The method of claim 32, further comprising linking said probe to the analyte.

* * * * *